United States Patent [19]
Thomaides et al.

[11] Patent Number: 5,563,252
[45] Date of Patent: Oct. 8, 1996

[54] POLYMERIZABLE SACCHARIDE MONOMERS WHICH CONTAIN A SINGLE, POLYMERIZABLE, α-METHYL STYRYL MOIETY

[75] Inventors: John S. Thomaides, Berkeley Heights; James Burkert, Rahway, both of N.J.; Rajeev Farwaha, Brampton, Canada; Robert W. R. Humphreys, Annandale; Paul M. Petersen, Three Bridges, both of N.J.

[73] Assignee: National Starch and Chemical Investment Holding Corporation, Wilmington, Del.

[21] Appl. No.: 461,478

[22] Filed: Jun. 5, 1995

[51] Int. Cl.$^6$ .................... C07H 1/00; C07H 5/06
[52] U.S. Cl. .................. 536/18.7; 536/22.1; 536/55.3
[58] Field of Search ................... 536/22.1, 18.7, 536/55.3

[56] References Cited

U.S. PATENT DOCUMENTS

| | | | |
|---|---|---|---|
| 2,891,944 | 6/1959 | Boettner | 260/211 |
| 4,843,154 | 6/1989 | Klein et al. | 536/4.1 |
| 5,194,639 | 3/1993 | Connor et al. | 554/66 |

FOREIGN PATENT DOCUMENTS

| | | |
|---|---|---|
| 0220676A1 | 10/1985 | Germany. |
| 0383023A2 | 8/1990 | Germany. |
| WO92/06984 | 4/1992 | WIPO. |
| WO92/08687 | 5/1992 | WIPO. |

OTHER PUBLICATIONS

The Aldrich Catalog 1994, Aldrich Chemical Company, p. 844.
Joachim Klein, "New Surfactant Polymers Based on Carbohydrates", Makromol. Chem. 191, 517–528 (1990).

Primary Examiner—Gary L. Kunz
Attorney, Agent, or Firm—William K. Wissing

[57] ABSTRACT

Polymerizable, saccharide-derived monomers are prepared in processes which utilize water as the reaction solvent and which preferably do not utilize a cosolvent. The saccharide monomers are prepared from a saccharide unit, an amine selected from the group consisting of $R^3NH_2$, where $R^3$ is selected from the group consisting of a $C_1$–$C_{18}$ alkyl group, H or $NH_2$, and a single, polymerizable, α-methyl styryl moiety. The saccharide monomers are useful in preparing polymers for use in freeze-thaw stable aqueous-based compositions which do not require conventional freeze-thaw solvents and colorimetrically detectable polymers which are used in treating aqueous systems.

12 Claims, No Drawings

5,563,252

POLYMERIZABLE SACCHARIDE MONOMERS WHICH CONTAIN A SINGLE, POLYMERIZABLE, α-METHYL STYRYL MOIETY

FIELD OF THE INVENTION

Polymerizable saccharide monomers are prepared in processes which utilize water as the reaction solvent and which preferably do not utilize a cosolvent in preparing the monomers. The monomers contain a single, polymerizable, α-methyl styryl moiety. The monomers are useful in preparing freeze-thaw stable latex coating compositions which do not require the use of volatile freeze-thaw additives and in preparing colorimetrically detectable polymers which are used in treating aqueous systems such as boiler water or steam generating systems, cooling water systems, gas scrubbing systems, pulp and paper mill systems, desalination systems, and downhole systems encountered during the production of gas, oil, and geothermal wells.

BACKGROUND OF THE INVENTION

Polysaccharides such as cellulose, starches, alginates, and pectins are extremely important commercially both in industrial applications and in consumer products. There is, therefore, a growing interest in the preparation of saccharide-derived monomers that can be used to prepare addition-type polymers containing saccharide functionality. The efficient preparation of saccharide-derived monomers has proved to be challenging however.

Simple elaboration of one of the available saccharide hydroxyl groups into a polymerizable group cannot, in general, be used to prepare mono-functional monomers because it is difficult to chemically distinguish the multiple hydroxyl substituents. For example, esterification of sucrose with methacryloyl chloride gives a mixture of sucrose mono-methacrylates and some sucrose dimethacrylates. The presence of even a small percentage of difunctional monomer can lead to the formation of gels upon polymerization, which in most cases is undesirable. A number of different approaches have been taken to either circumvent this problem or otherwise selectively prepare mono-functional saccharide-derived monomers.

The use of protecting groups to block the reactivity of the excess hydroxyl groups is a classic strategy for the synthesis of saccharide-derived monomers. There are numerous reported syntheses in which the saccharide to be converted into a monomer is per-acetylated, and then a polymerizable functionality is elaborated onto the anomeric carbon. Similarly, a protecting group strategy can be used to mask all but one of the hydroxyl groups, which can then be esterified with an acrylic or a methacrylic acid derivative or converted to an allyl ether. In the latter case, the allyl ether can be hydrosilated with poly(dimethylsiloxane-co-methylsiloxane) to give a polysiloxane with pendant saccharide functionality. The principal drawback of the protecting group strategy is the need to introduce and then remove the protecting groups.

Other workers have sought to elaborate the anomeric carbon into a polymerizable group using a glycosidase enzyme catalyst. The enzyme β-galactosidase was used to transfer lactose or o-nitrophenyl β-D-galactopyranoside to 2-hydroxyethyl acrylate or 2-hydroxyethyl methacrylate. Apparently, the desired galactopyranoside monomers could be obtained without using protecting groups. A potential drawback of this synthesis is that the saccharide is attached to the monomer (and, later, the polymer backbone) by an acid sensitive glycosidic linkage.

Enzymes have also been used to selectively esterify a single hydroxyl of a saccharide. For example, lipase or protease enzymes have been used to transesterify an active ester of acrylic acid such as vinyl acrylate with saccharides or saccharide derivatives. High conversions to predominantly monofunctional monomer in which only the primary hydroxyl of the saccharide is acryloylated are reported.

An alternative strategy to selectively esterifying a single hydroxyl group with an acrylate ester is to start with a saccharide molecule that contains a single functional group that is either significantly more reactive than a hydroxyl group, or reacts in a different manner. One such approach involves the condensation of amino saccharides such as glucosamine or 1-amino-1-deoxy-D-glucitol with acrylic or methacrylic anhydride. Exclusive formation of the corresponding (meth)acrylamide is expected because of the high reactivity of the single amino substituent relative to the many hydroxyl groups.

Another approach that exploits saccharide functionality other than hydroxyl groups involves the condensation of amine containing monomers with aldonic acid lactones. For example, condensation of p-vinylbenzylamine with δ-glucono-lactone gives N-p-vinylbenzyl gluconamide. The great advantage of this approach is that difunctional monomer is not a possible side-product of the synthesis. Primary amine containing monomers, however, are not readily available commercially.

Various alkyl-amino substituted mono- and disaccharides have been obtained by reductive amination of reducing mono- and disaccharides with $C_4$–$C_{10}$ alkyl amines. Subsequent coupling of the alkylamino substituted mono- or disaccharides with a vinyl substituted isocyanate was carried out at low temperature in aqueous systems or in organic solvents. However, due to the nature of the vinyl moiety present in the substituted isocyanate, these saccharide monomers can homopolymerize, which is undesirable in many cases.

It is apparent that significant efforts have been expended to develop polymerizable, saccharide-derived monomers and methods for preparing same. However, the methods and/or monomers disclosed heretofore are either impracticable, or suffer deficiencies of crosslinking due to their multifunctionality, or can homopolymerize. In certain applications, it would be desirable, then, to prepare polymerizable, saccharide-derived monomers which are substantially monofunctional and which will not homopolymerize.

SUMMARY OF THE INVENTION

The present invention is directed to polymerizable, saccharide monomers which comprise a single, polymerizable, α-methyl styryl moiety and to methods for preparing the saccharide monomers. The methods used to prepare the saccharide monomers preferably utilize only water as the reaction solvent and preferably are free of a cosolvent. In one embodiment, the process comprises mixing together, in water and in the absence of a cosolvent a saccharide of structure (I) with an amine of the formula $R^3NH_2$, where $R^3$ may be $C_1$–$C_{18}$ alkyl, H or $NH_2$. The admixture of the saccharide and the amine are contacted with pressurized hydrogen, in the presence of a Group VIIIB metal catalyst and under conditions effective to produce an amino saccharide of structure (11). The amino saccharide is reacted with 3-isopropenyl-α,α-dimethylbenzylisocyanate to form a saccharide monomer of structure (III).

DETAILED DESCRIPTION OF THE INVENTION

As used herein, the term "saccharide" is intended to include reducing sugars, oligosaccharides and polysaccharides, as those terms are known to one skilled in the art. The terms "saccharide monomers" and "polymerizable saccharide monomers" are used interchangeably herein.

In one embodiment, the present invention is directed to a process for preparing polymerizable, saccharide monomers, the process comprising:

(a) mixing together, in water and in the absence of a cosolvent,
  (i) a saccharide of structure (I);

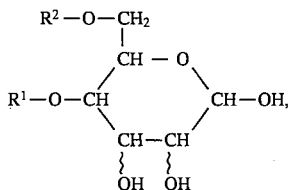

wherein, $R^1$, is H or is represented by structure I(a)

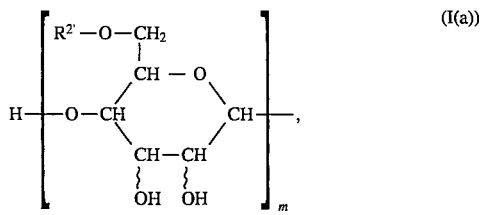

$R^2$, is H, or is represented by structure I(a) or structure I(b)

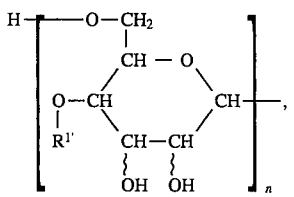

wherein $R^{1'}$, is H or is represented by structure I(a), $R^{2'}$ is H or is represented by structure I(a) or structure I(b), and m and n are greater than or equal to 0, and (ii) an amine selected from the group consisting of $R^3NH_2$, where $R^3$ is selected from the group consisting of a $C_1$–$C_{18}$ alkyl group, H or $NH_2$, thereby producing an aqueous admixture of the saccharide and the amine, (b) contacting the aqueous admixture of the saccharide and the amine with hydrogen, under pressure, in the presence of a Group VIIIB metal catalyst and under conditions effective to produce an amino saccharide of structure (II);

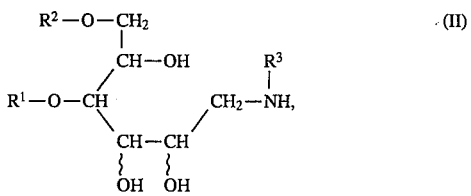

wherein $R^1$, $R^2$, $R^3$, $R^{1'}$, $R^{2'}$, m and n are as above, (c) adding 3-isopropenyl-α,α-dimethylbenzylisocyanate to the amino saccharide; and (d) mixing the amino saccharide and the 3-isopropenyl-α,α-dimethylbenzylisocyanate under conditions effective to produce a saccharide monomer of structure (III),

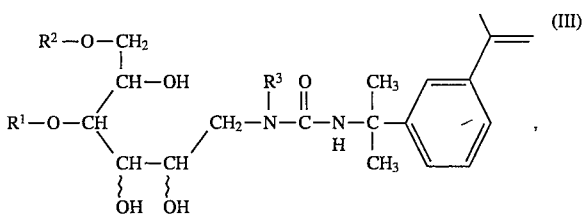

wherein $R^1$, $R^2$, $R^3$, $R^{1'}$, $R^{2'}$, m and n are as above; and wherein the catalyst and excess amine are removed from the reaction.

In preferred embodiments, the methods of preparing the saccharide monomers exclude the use of a cosolvent with the water throughout the process for preparing the saccharide monomers. Cosolvent, as used herein, is intended to include organic solvents, such as alcohols, ketones, and polar aprotic solvents such as dimethyl sulfoxide, dimethyl formamide and pyridine. Cosolvent, as used herein, is also intended to include excess amine utilized in the process to the extent that the amine is present in amounts effective to function as a solvent in the process.

In forming the admixture of the saccharide of structure (I) and the amine, the saccharide and the amine are mixed together in water and in the absence of a cosolvent until an admixture thereof is formed. In preferred embodiments, the saccharide is added to water and blended until the saccharide is either dissolved in the water or homogeneously dispersed in the water. The saccharide/water mixture is added to the amine and blended, preferably at temperatures less than about 10° C., for a time effective to form an admixture of the saccharide and the amine, typically at least about one hour.

Generally, the saccharides used to prepare the monomers of the present invention may be reducing sugars or may be composed of glycosyl units connected by glycosidic linkages. These saccharides have one reducing end-group. They can be linear or branched, and they may be composed of a single type of glycosyl unit or they may be composed of two or more different types of glycosyl units. Exemplary saccharides according to the present invention include, without limitation, starches, hydrolyzed starches, glucose, galactose, maltose, lactose, maltodextrins, corn syrup solids, cellulose, hydrolyzed cellulose, dextran, hydrolyzed dextran, guar gum, hydrolyzed guar gum, locust bean gum and hydrolyzed locust bean gum. Such starches include, for example, corn, potato, tapioca and rice starches. The saccharides used to prepare the polymers of the present invention are represented by structure (I), where $R^1$ and $R^2$ are as set forth herein above. In particularly preferred embodiments, the polysaccharide is a starch represented by structure (I) where $R_1$ is represented by structure I(a) and $R^2$ is represented by structure I(a) or is H. The amine used in the present invention is selected from the group consisting of $R^3NH_2$, where $R^3$ may be a $C_1$–$C_{18}$ alkyl group, H or $NH_2$. Preferably, $R^3$ is a $C_1$–$C_3$ alkyl group. More preferably, the amine is methyl amine.

The admixture of the saccharide and the amine are contacted with hydrogen, under pressure and in the presence of a Group VIIIB metal catalyst, for a period of time effective to produce an amino saccharide of structure (II). Preferably, the admixture of the saccharide and the amine is placed in a reactor with the Group VIIIB metal catalyst and the contents brought to a temperature adequate to facilitate the formation of the amino saccharide. Preferably, the temperature is from 10° C. to 100° C., more preferably from 40°

C. to 60° C. The metal catalyst utilized may comprise any of the Group VIII metals, with nickel, palladium, platinum and ruthenium being preferred. Particularly preferred catalysts are Raney nickel catalyst and supported nickel catalysts such as those available from United Catalysts Inc., Louisville, Ky. under the trade name G-49B. The reactor is purged with nitrogen or a comparable inert gas and pressurized with hydrogen. The pressure will be effective to facilitate the reaction between the saccharide and the amine. Generally, the higher the pressure, the quicker is the reaction. Preferably the pressure will be at least about 100 psi, more preferably at least about 700 psi. The contents of the reactor are mixed until the reaction is substantially completed. Typically, the contents are mixed for about 8 to 20 hours, preferably about 12 hours. The temperatures and pressures noted above are not intended to limit the scope of the claims appended hereto. As one skilled in the art will recognize, once armed with the present specification, the conditions of temperature and pressure may be selected such that the reaction rate and product yield may be optimized.

After the amino saccharide has been formed, the catalyst must be removed therefrom. While one skilled in the art will appreciate that there are various means to remove the catalyst, in preferred embodiments, the catalyst is removed via filtration. The amino saccharide may be further concentrated to a solid, if so desired, and redissolved in water prior to forming the saccharide monomers of the present invention. Preferably, after the catalyst is removed, 3-isopropenyl-α,α-dimethylbenzylisocyanate is added to the amino saccharide and the two are mixed under conditions effective to produce a saccharide monomer of structure (III).

In preferred embodiments, a stoichiometric excess of the amine is mixed with the saccharide to facilitate the reaction of the saccharide with the amine. Without intending to be limited by the following, as the amino saccharide is formed, a less preferred reaction between the amino saccharide and the saccharide is believed to take place. A stoichiometric excess of the amine is used to facilitate the preferential reaction between the saccharide and the amine. It is preferred that the excess amount of amine used in the process be minimized, as any excess amine must be removed prior to the reaction of the amino saccharide with the 3-isopropenyl-α,α-dimethylbenzylisocyanate. In addition, the amine is not used in excess amounts to the extent that it will function as a solvent in the process. Preferably, the saccharide and amine are used at molar ratios of 1:1 to 1:2, preferably from 1:1 to 1:1.5.

The amino saccharide and the 3-isopropenyl-α,α-dimethylbenzylisocyanate are preferably combined in molar ratios ranging from about 0.8:1 to about 1.2:1, respectively. In more preferred embodiments, the amino saccharide and the 3-isopropenyl-α,α-dimethylbenzylisocyanate are combined in equimolar amounts. The monomers of the present invention are unique in that they will copolymerize readily with acrylic monomers such as (meth)acrylates, sulfonic monomers such as sodium methallyl sulfonate, and acrylamido monomers, yet will not homopolymerize due to the nature of the α-methyl styryl moiety. This property of the saccharide monomers is particularly advantageous where selective copolymerization with the respective comonomer is desired, without the formation of saccharide homopolymers. This not only provides homogeneous copolymers, but also allows one to minimize the amount of saccharide monomer required to prepare the particular copolymer which contains the saccharide monomers. As the saccharide monomers are monofunctional, i.e., they contain a single, polymerizable α-methyl styryl moiety, crosslinking and gelling are avoided during polymerization.

The saccharide monomers of the present invention have been found to be useful in preparing aqueous-based coating compositions which are freeze-thaw stable, even in the absence of conventional volatile freeze-thaw additives, such as ethylene or propylene glycols. Such coating compositions include freeze-thaw stable latex binders, freeze-thaw stable latex paint compositions and freeze-thaw stable, aqueous-based, adhesive compositions. Such latex compositions do not require the use of conventional freeze-thaw solvents.

The saccharide monomers also have been found to be useful in preparing colorimetrically detectable polymers which are used in treating aqueous systems such as boiler water or steam generating systems, cooling water systems, gas scrubbing systems, pulp and paper mill systems, desalination systems, and downhole systems encountered during the production of gas, oil, and geothermal wells. The water treatment polymers have the saccharide monomer covalently attached to the polymer backbone. Upon the contacting the saccharide-modified water treatment polymer with a photoactivator, the level of the saccharide, and thus the level of the water treatment polymer, can be determined at concentrations of less than 100 ppm.

The following examples are in no way meant to limit the breadth of the claims appended hereto but are submitted merely to present preferred embodiments of the present invention.

EXAMPLE 1

PREPARATION OF SACCHARIDE MONOMER

A: Reductive Amination

α-D-Lactose monohydrate (100 g, 0.28 mole) was dissolved in water (150 ml) with the aid of stirring and heating. The solution was cooled to room temperature then added over two hours to a solution of methylamine (40% w/w in water, 43 g, 0.55 mole) in water (50 ml) while stirring under nitrogen gas and holding at 0 to 10° C. The resultant mixture was stirred for a further one hour, and then it was poured into a pressure vessel and United Nickel Catalyst G-49B (10 g) was added. The pressure vessel was then heated at 55° C. under an atmosphere of 700 p.s.i. hydrogen gas for 24 hours. After this time the reaction vessel was depressurized and the catalyst was removed by filtration through filter paper and then through Celite. A small sample of the flitrate was evaporated to dryness on a vacuum pump then titrated versus dilute hydrochloric acid to determine that the reaction was complete. The rest of the sample was evaporated to low volume, to ensure removal of excess methylamine, after which it was treated directly with 3-isopropenyl-α,α-dimethylbenzylisocyanate as detailed below.

B. Urea Formation

To a solution of N-methyl-D-lactamine (95 g, 0.27 mol) in water (350 ml) was added 3-isopropenyl-α,α-dimethybenzylisocyanate (54 g, 0.27 mole) and the resulant two phase mixture was vigorously stirred for ten hours. The course of the reaction was monitored by observance of the disappearance of the isocyanate peak at ~2250 cm$^{-1}$ in an infra-red spectrum obtained of the reaction mixture. A small amount of an off-white precipitate formed and was removed by filtration. Unreacted aminosaccharide (<5%), as determined by titration of the reaction mixture versus dilute hydrochloric acid, was removed by the addition of Amberlite IR-120 (plus) ion exchange resin and stirring for four hours. The resin was then filtered and the solution was freeze dried to yield a white solid (143 g, 96%) whose NMR data was consistent with the structure proposed.

Additional saccharide monomers were prepared according to the above procedure, wherein the α-D-lactose monohydrate was replaced with glucose, galactose, maltose, corn syrup solids with DE=24 and maltodextrin with DE=10, respectively.

We claim:

1. A process for preparing polymerizable, saccharide monomers, the process comprising:
   (a) mixing together, in water and in the absence of a cosolvent,
      (i) a saccharide of structure (1);

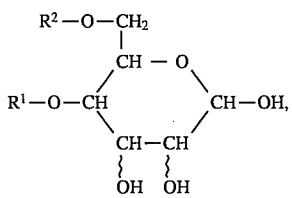

wherein, $R^1$ is H or is represented by structure I(a)

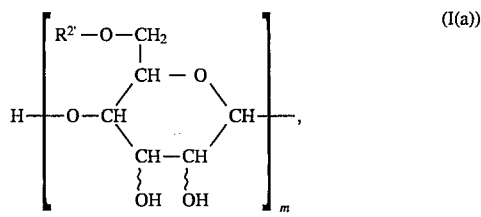

$R^2$ is H, or is represented by structure I(a) or structure I(b)

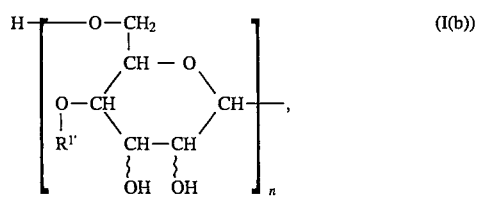

wherein $R^{1'}$ is H or is represented by structure I(a), $R^{2'}$ is H or is represented by structure I(a) or structure I(b), and wherein m and n are greater than or equal to 0, and
      (ii) an amine selected from the group consisting of $R^3NH_2$, where $R^3$ is selected from the group consisting of a $C_{1-C18}$ alkyl group, H or $NH_2$, thereby producing an aqueous admixture of the saccharide and the amine,
   (b) contacting the aqueous admixture of the saccharide and the amine with hydrogen, under pressure, in the presence of a Group VIIIB metal catalyst and under conditions effective to produce an amino saccharide of structure (II);

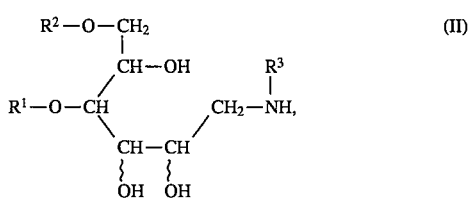

wherein $R^1$, $R^2$, $R^3$, $R^{1'}$, $R^{2'}$, m and n are as above,
   (c) adding 3-isopropenyl-α-α-dimethylbenzylisocyanate to the amino saccharide; and
   (d) mixing the amino saccharide and the 3-isopropenyl-α,α-dimethylbenzylisocyanate under conditions effective to produce a saccharide monomer of structure (III),

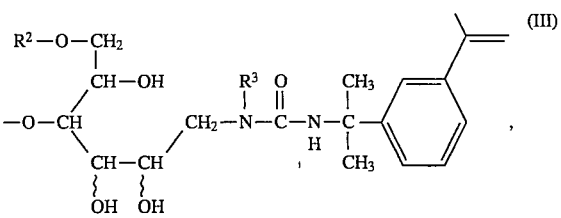

wherein $R^1$, $R^2$, $R^3$, $R^{1'}$, $R^{2'}$, m and n are as above; and wherein the catalyst and excess amine are removed from the reaction.

2. The process according to claim 1 wherein $R^1$ is represented by structure I(a), $R^2$ is H or is represented by structure I(a) and $R^{2'}$ is H or represented by structure I(a).

3. The process according to claim 1 wherein $R^3$ is a $C_1$-$C_3$ alkyl group.

4. The process according to claim 1 wherein $R^3$ is a methyl group.

5. The process according to claim 1 wherein the aqueous admixture of the saccharide and the amine is contacted with the hydrogen at a pressure of at least 100 psi and the Group VIIIB catalyst is selected from the group consisting of nickel, platinum, palladium and ruthenium.

6. The process according to claim 1 wherein the amine is mixed with the saccharide in a stoichiometric excess relative to the saccharide.

7. The process according to claim 6 wherein the amino saccharide and the 3-isopropenyl-α,α-dimethylbenzylisocyanate are present in molar ratios ranging from about 0.8:1 to 1.2:1, respectively.

8. The process according to claim 1 wherein the amino saccharide and the 3-isopropenyl-α,α-dimethylbenzylisocyanate are present in molar ratios ranging from about 0.8:1 to 1.2:1, respectively.

9. A saccharide monomer having structure (III)

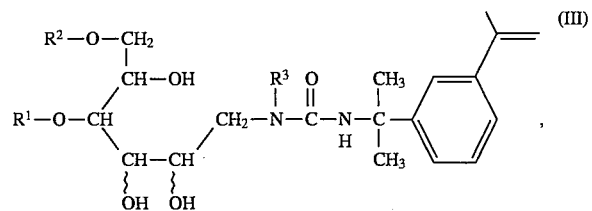

wherein, $R^1$ is H or is represented by structure I(a)

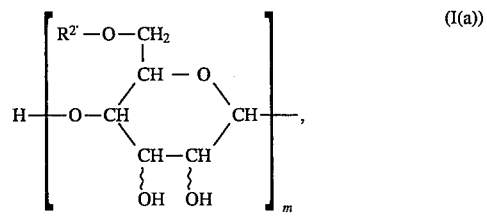

$R^2$ is H, or is represented by structure I(a) or structure I(b)

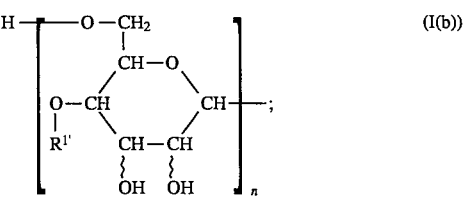

wherein $R^{1'}$ is H or is represented by structure I(a),
$R^{2'}$ is H or is represented by structure I(a) or structure I(b), and wherein m and n are greater than or equal to 0.

10. The saccharide monomer according to claim 9 wherein $R^1$ is represented by structure I(a), $R^2$ is H or is represented by structure I(a) and $R^{2'}$ is H or represented by structure I(a).

11. The saccharide monomer according to claim 9 wherein $R^3$ is a $C_1$–$C_3$ alkyl group.

12. The saccharide monomer according to claim 9 wherein $R^3$ is a methyl group.

* * * * *